US00PP19275P2

(12) United States Plant Patent
Hambali

(10) Patent No.: US PP19,275 P2
(45) Date of Patent: Sep. 30, 2008

(54) *CALATHEA* PLANT NAMED 'TWYCA0043'

(50) Latin Name: ***Calathea* hybrid**
Varietal Denomination: TWYCA0043

(75) Inventor: Gregori Garnadi Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/974,535

(22) Filed: Oct. 15, 2007

(51) Int. Cl.
*A01H 5/00* (2006.01)

(52) U.S. Cl. ..... Plt./375

(58) Field of Classification Search ..... Plt./375
See application file for complete search history.

*Primary Examiner*—Annette H Para
(74) *Attorney, Agent, or Firm*—Jondle & Associates, P.C.

(57) ABSTRACT

A new *Calathea* plant particularly distinguished by upright, wider than tall, dense leafy growth habit with paper-white bracted inflorescences which are held above and among the foliage, glossy, elliptical leaves with alternating bars of dark and lighter green which follow the primary veins and a thin band of silver green along the margin of the leaf, is disclosed.

1 Drawing Sheet

Genus and species: *Calathea* hybrid.
Variety denomination: 'TWYCA0043'.

BACKGROUND OF THE NEW PLANT

The present invention comprises a new and distinct cultivar of *Calathea,* botanically known as *Calathea* hybrid, and hereinafter referred to by the cultivar name 'TWYCA0043'. The new cultivar originated from a hybridization made in Bogor, Indonesia. The female parent was an unknown individual plant of *Calathea loesenerii* (patent status unknown). The male parent was a *Calathea roseopicta* plant named 'Illustris' (not patented).

A single plant selection was chosen for further evaluation and for asexual propagation in August 2000.

The new cultivar was first propagated in Apopka, Fla. and has been asexually reproduced repeatedly by sucker and tissue culture in Apopka, Fla. over four generations. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1. Glossy, elliptical leaves, with alternating bars of dark and lighter green which follow the primary veins and a thin band of silver green along the margin of the leaf;
2. Upright, wider than tall, dense leafy growth habit; and
3. Long-lasting paper-white inflorescences displayed above and among the foliage.

DESCRIPTION OF PHOTOGRAPH

This new *Calathea* plant is illustrated by the accompanying photograph which shows the overall plant habit and foliage of the plant; the colors shown are as true as can be reasonably obtained by conventional photographic procedures.

DESCRIPTION OF THE NEW CULTIVAR

The following detailed description sets forth the distinctive characteristics of 'TWYCA0043'. The data which define these characteristics were collected from asexual reproductions carried out in Apopka, Fla. The data were obtained in December 2005 from 14-month old plants grown in 6-inch pots from a 13-week-old tissue culture derived liner. The plants were grown in a greenhouse with fiberglass panel siding with inflated double poly roof with a modine heating, fan and pad cooling system. The average day temperature ranged from 24° C. to 35° C. and the average night temperature ranged from 18° C. to 24° C. The light level was about 1500 FC. No photoperiodic treatments or growth retardants were used. Color references are to The Royal Horticultural Society Colour Chart, 2001 edition.

DETAILED BOTANICAL DESCRIPTION OF THE NEW PLANT

Classification:
- *Family.*—Marantaceae.
- *Botanical name.*—*Calathea* hybrid.
- *Common name.*—*Calathea.*

Parentage:
- *Female parent.*—An unknown individual plant of *Calathea loesenerii* (patent unknown).
- *Male parent.*—'Illustris' a *Calathea roseopicta* plant (not patented).

Growth:
- *General.*—Tropical flowering potted plant; plant is suitable for use in shaded tropical landscapes including
- *Time to flower.*—14 months to finish starting from a 13-week old liner from tissue culture.
- *Appropriate container.*—15 cm to 20 cm pots; suitable for use in shaded tropical landscapes and indoors.

Plant description:
- *Life cycle.*—Herbaceous perennial.
- *Habit.*—Upright, wider than tall, inverted triangle, densely leafy; inflorescences upright and slightly above and among the foliage in the center of the plant; upright whorls of leaves arise from underground rhizome; rhizomaceous.

*Vigor.*—Typical of *Calathea;* progressive and consistent growth.

*Height* (*soil line to the top of the leaf canopy*).—31.0 cm to 36.0 cm.

*Spread* (*including flowers*).—55.0 cm to 61.0 cm.

*Root color.*—RHS N199B (dark brown); tips RHS 145D to RHS 155A.

*Temperature tolerances.*—High temperature of 105° F. to a low temperature of 40° F.

Branches:

*Branching habit.*—Basal branching, rhizomaceous.

*Number.*—10 basal branches.

*Length.*—Variable depending upon age.

*Lateral branch diameter.*—1.1 cm.

Stems (rhizomes):

*Description.*—Cylindrical, round in traverse section.

*Aspect.*—Horizontal, underground rhizome becoming upturned, vertical at tip.

*Strength.*—Thick, tough and fibrous.

*Internode length.*—0.5 cm to 2.2 cm.

*Color.*—RHS 173D with RHS 186B to RHS 186C tinged with RHS 147C.

Leaves:

*Arrangement.*—Alternate, closely spaced in vertical ranks, rosette, with one to three leaves per lateral branch depending on age of the branch.

*Shape.*—Simple, elliptical.

*Apex.*—Acuminate to cuspidate.

*Base.*—Obtuse.

*Margin.*—Entire, somewhat undulate.

*Size.*—Length: 21.0 cm to 25.0 cm. Width: 11.0 cm to 13.5 cm.

*Color.*—Immature leaf: Upper surface: Leaf Margin RHS 147A with RHS196C (silver-green) band; leaf center RHS 146C (medium green) with bars of RHS 147A (dark green). Lower surface: RHS N186C. Mature leaf: Upper surface: Leaf margin darker and greener than, but closest to RHS 147A with RHS 196D (silver-green) band; leaf center RHS 146B (medium green) with bars that are darker than, but closer to RHS 147A (dark green). Lower surface: RHS N186C.

*Venation.*—Type: Pinnate. Color: Upper surface: RHS 147A midrib and primary veins. Lower surface: RHS N186C; midrib RHS N186C tinged with RHS 183B.

*Texture.*—Upper surface: Glossy to shiny, concave between primary veins resulting in a slightly texture look. Lower surface: Matte, dull.

*Surface pubescence.*—Absent.

Petiole:

*Length* (*from basal attachment at rhizome to base of leaf*).—20.0 cm to 25.0 cm.

*Diameter.*—0.5 cm.

*Texture.*—Smooth, glossy.

*Color.*—RHS N186C.

*Petiole sheath.*—Encircles the rhizome and extends up the petiole to within 14.0 cm of the base of the leaf. Color: Outside: RHS N186C with RHS 183C. Inside: RHS N186C tinged with RHS 147B. Texture: Inside smooth and shiny.

*Cataphylls.*—Shape: Lanceolate. Apex: Acute. Base: Sessile, clasping rhizome. Length: 8.0 cm to 10.0 cm. Width (flattened): 1.2 cm. Color: Outside: RHS N186C with RHS 183C. Inside: RHS N186C with RHS 183C tinged with RHS 147B. Texture: Outside covered with short, fine pubescence; inside smooth, shiny.

Geniculum:

*General.*—Orientation of the leaf to the petiole is variable as the geniculum bends; during the night and early morning the geniculum is straight, and the leaf is held nearly vertical above the foliage; during the day, the geniculum is bent, and the leaf is held about 90° to the petiole.

*Length.*—2.8 cm.

*Width.*—0.51 cm.

*Color.*—RHS 177A tinged with RHS N186C.

Flower bud:

*Size.*—Length: 1.5 cm. Diameter: 0.25 cm.

*Shape.*—Elongated, elliptic.

*Color.*—Translucent white becoming RHS 200A (dark brown) without opening.

Inflorescence:

*Flowering season.*—Spring and fall.

*Arrangement.*—Inflorescence emerges slightly off-center of the whorl of leaves; branch spikes covered by colorful bracts atop a tall upright spike.

*Inflorescence type.*—Tall, upright, terminally bracted spike; bracts arranged in closely spaced vertical ranks occupying the upper 6.0 cm of the spike; inflorescence persistent after senescence.

*Inflorescence height.*—40.0 cm.

*Inflorescence width.*—6.8 cm from tip to tip of bracts across top of inflorescence.

*Quantity of flowers per inflorescence.*—Flowers vestigal.

*Quantity of flowers and buds per plant.*—About 10 spikes present.

*Fragrance.*—Absent.

Peduncle:

*Length.*—33.0 cm.

*Diameter.*—0.38 cm.

*Angle.*—Straight upright.

*Strength.*—Tough flexible.

*Texture.*—Smooth, glossy.

*Color.*—RHS N186C with RHS 183B.

Bracts:

*General.*—Terminal bracts uppermost on raceme, subtended by fertile bracts with underlying branch spikes.

*Terminal bracts.*—Quantity: 7. Length: 4.0 cm. Width: 2.1 cm. Shape: Ovate, slightly cupped upward. Apex: Acute. Base: Acute. Margin: Entire, smooth. Color: Upper surface: Paper white with streaks of RHS 146D toward the tip. Lower surface: RHS 155C (white), tinged with RHS N78C (pink) with streaks of RHS 146D (green) towards the tip. Texture: Upper surface: Smooth. Lower surface: Smooth.

*Fertile bracts.*—Quantity: 18. Length: 2.5 cm. Width (flattened): 3.0 cm. Shape: Broadly obovate. Apex: Emarginate. Base: Acute. Margin: Entire, smooth. Color: Upper surface: Translucent paper white, base RHS 155D. Lower surface: RHS 155C occasionally tinged with RHS N78C; base of bract RHS 155D. Texture (both surfaces): Smooth.

Reproductive organs: Has not been observed.

Fruit and seed set: Has not been observed.

Disease and insect resistance: Resistance and susceptibility is typical of the species.

COMPARISON WITH PARENTAL AND COMMERCIAL CULTIVARS

'TWYCA0043' differs from the female parent *Calathea loesenerii* (patent status unknown) in that 'TWYCA0043' has paper-white bracted inflorescences, while the female parent has pale pink to white bracted inflorescences. Additionally, 'TWYCA0043' has broadly ovate leaves with attractive patterns, while the female parent has narrow, long leaves, that are mostly green and faintly patterned.

'TWYCA0043' differs from the male parent a *Calathea roseopicta* named 'Illustris' (not patented) in that 'TWYCA0043' has paper-white bracted inflorescences which are displayed above and among the foliage, while 'Illustris' has green, short scaped, inconspicuous bracts which are held mostly among and below the foliage. Additionally, 'TWYCA0043' has narrower and more numerous leaves, while 'Illustris' has wider and less numerous leaves that are a darker green than 'TWYCA0043'.

'TWYCA0043' differs from the commercial cultivar *Calathea roseopicta* (not patented) in that 'TWYCA0043' has paper-white bracted inflorescences which are displayed above and among the foliage, while *Calathea roseopicta* has green, short scaped, inconspicuous bracts which are held mostly among and below the foliage. Additionally, 'TWYCA0043' has leaves with dark green bars which follow the primary veins against a lighter green background, while *Calathea roseopicta* has leaves which are entirely very dark green with a marginal band of silver-green and a silver green midrib. Additionally, 'TWYCA0043' has not been observed to fully develop, while *Calathea roseopicta* has flowers which are functional and fertile.

I claim:

1. A new and distinct cultivar of *Calathea* plant as shown and described herein.

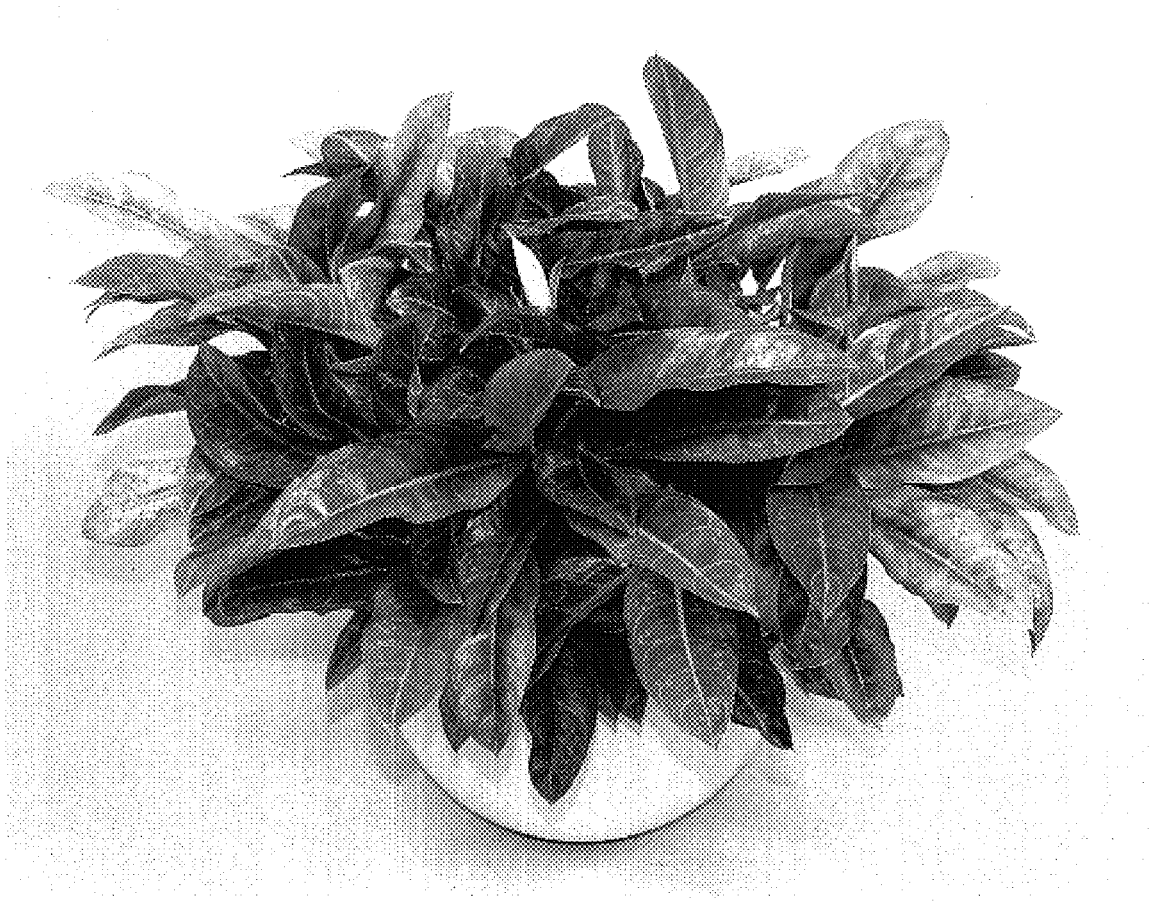

* * * * *